United States Patent
Anhoeck et al.

(10) Patent No.: US 9,522,040 B2
(45) Date of Patent: Dec. 20, 2016

(54) ENDOSCOPIC SURGICAL INSTRUMENT

(71) Applicant: Ovesco Endoscopy AG, Tuebingen (DE)

(72) Inventors: Gunnar Anhoeck, Reutlingen, DE (US); Sebastian Menge, Tuebingen (DE); Chi-Nghia Ho, Stuttgart (DE); Marc O. Schurr, Tuebingen (DE)

(73) Assignee: OVESCO ENDOSCOPY AG, Tuebingen (DE)

( * ) Notice: Subject to any disclaimer, the term of this patent is extended or adjusted under 35 U.S.C. 154(b) by 0 days.

(21) Appl. No.: 13/846,755

(22) Filed: Mar. 18, 2013

(65) Prior Publication Data

US 2013/0296842 A1    Nov. 7, 2013

(30) Foreign Application Priority Data

Mar. 19, 2012 (DE) .................. 10 2012 102 271

(51) Int. Cl.
| | | |
|---|---|---|
| *A61B 18/14* | (2006.01) | |
| *A61B 18/18* | (2006.01) | |
| *A61B 18/00* | (2006.01) | |
| *A61B 17/00* | (2006.01) | |

(52) U.S. Cl.
CPC .......... *A61B 18/18* (2013.01); *A61B 18/1477* (2013.01); *A61B 2017/0088* (2013.01); *A61B 2018/0097* (2013.01); *A61B 2018/00166* (2013.01); *A61B 2018/00196* (2013.01); *A61B 2018/1475* (2013.01); *A61B 2218/002* (2013.01)

(58) Field of Classification Search
CPC .............. A61B 18/149; A61B 18/1485; A61B 2018/1412; A61B 2018/1422; A61B 2018/1425; A61B 2018/1427; A61B 2018/144; A61B 2018/00196
USPC .......................................................... 606/46
See application file for complete search history.

(56) References Cited

U.S. PATENT DOCUMENTS

| | | | |
|---|---|---|---|
| 4,719,914 A * | 1/1988 | Johnson ............... | A61B 18/082 604/35 |
| 4,848,339 A * | 7/1989 | Rink et al. ......................... | 606/7 |
| 5,403,311 A * | 4/1995 | Abele et al. ..................... | 606/49 |

(Continued)

FOREIGN PATENT DOCUMENTS

| | | |
|---|---|---|
| EP | 1834598 A1 | 9/2007 |
| EP | 2 156 801 A1 | 2/2010 |
| EP | 2156801 A1 | 2/2010 |

OTHER PUBLICATIONS

Extended European Search Report dated Jul. 11, 2013 in European Patent Application No. 13159778.3.

(Continued)

*Primary Examiner* — Jaymi Della
(74) *Attorney, Agent, or Firm* — TechLaw LLP

(57) ABSTRACT

What is disclosed is an endoscopic surgical instrument with a hose-shaped outside jacket, in which a likewise hose-shaped inside jacket is supported relatively displaceable, on whose distal end section a sleeve or shaft-shaped instrument head is formed or mounted. In the instrument head is fixed a needle-shaped RF electrode electrically-insulated, whose electrical supply line is routed through the inside jacket, and which projects freely beyond the distal end of the instrument head in the axial direction. In the instrument head is formed a flush channel, extending at least axially, opening at both instrument head ends.

10 Claims, 3 Drawing Sheets

SECTION A - A

(56) References Cited

U.S. PATENT DOCUMENTS

Figure 1:
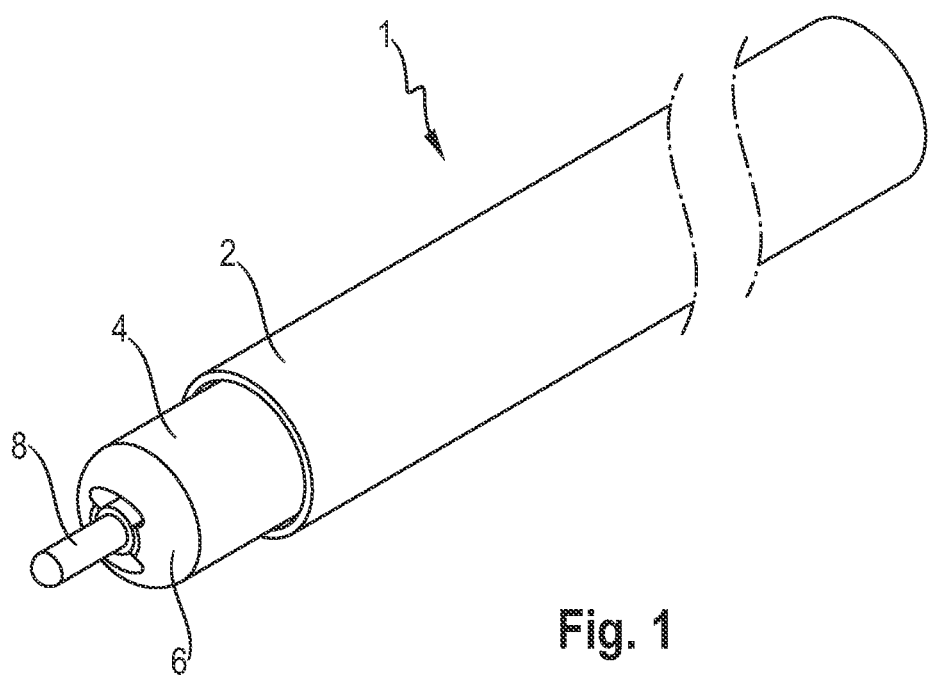

| | | | |
|---|---|---|---|
| 5,662,647 A * | 9/1997 | Crow et al. | 606/41 |
| 6,193,717 B1 * | 2/2001 | Ouchi | 606/49 |
| 6,295,990 B1 | 10/2001 | Lewis et al. | |
| 7,056,283 B2 * | 6/2006 | Baror et al. | 600/114 |
| 2005/0177151 A1 * | 8/2005 | Coen et al. | 606/41 |
| 2007/0038213 A1 * | 2/2007 | Machiya | A61B 18/1492 606/45 |
| 2008/0045785 A1 * | 2/2008 | Oyatsu | A61B 18/1492 600/104 |
| 2009/0005774 A1 * | 1/2009 | Fernald | 606/41 |
| 2009/0254083 A1 | 10/2009 | Wallace et al. | |
| 2012/0035605 A1 * | 2/2012 | Tegg et al. | 606/41 |

OTHER PUBLICATIONS

German Search Report in Application No. 10 2012 102271.2, Oct. 29, 2012.

* cited by examiner

ENDOSCOPIC SURGICAL INSTRUMENT

This invention concerns an endoscopic surgical instrument of the TFT design type, and in particular an endoscopic surgical instrument with a fluid-flushed RF electrode.

BACKGROUND OF THE INVENTION

In modern minimum-invasive surgery, surgical instruments with TFT construction design are increasingly employed, where RF electrodes are subjected to an RF current in monopolar or bipolar arrangement, in order to cut and/or weld/seal an organ tissue. In order to keep the access channel for the surgical instrument as small as possible, and nevertheless to permit a sufficiently good view of the operation location, it is important to keep the operation location as clean as possible and free from tissue particles and/or blood. In this respect, the flushing of the operation location, in particular with minimum-invasive surgical technology, is gaining increasingly in importance.

STATE OF THE ART

From EP 1 834 598 A1 an endoscopic surgical instrument of the existing kind is known. This has one supply shaft, at whose proximal end (turned away from the body) a handgrip/instrument grip is arranged and at whose distal end (turned towards body) a plug-shaped insertion part is provided, which is inserted into the supply shaft. The insertion part has a central through-bore, as well as at least one decentralized flush transition channel.

In the supply shaft a pin or pin-shaped RF electrode is axially slid, which is connected over a current line within the supply shaft with the instrument grip. In this case, the RF electrode is inserted into a guide sleeve that is movable sliding on the supply shaft and in which a number of decentralized axial through-bores are formed. However, this guide sleeve serves not only as a distal slide support for the RF electrode, but also as an axial stop to limit of the axial advance movement of the RF electrode. Expressed in other words, the guide sleeve, in case of advancing the RF electrode, comes axially into the system through the central through-bore of the inserted part and stops this feed movement in this case.

Although, as a result of this construction, a supply of flush medium for the operation location is possible, the flush medium must pass through both the transition channels in the guide sleeve, as well as in the inserted part, which represent a large flow obstacle. The fluid pressure is therefore not very high at the operation location.

SUMMARY OF THE INVENTION

Faced with this problem, it is the object of this invention to appropriate an endoscopic surgical instrument which indicates an increased functionality. A special goal is to improve the flush property of the endoscopic surgical instrument, in particular in the case of a TFT construction design.

This object is solved by an endoscopic surgical instrument with the features of the patent Claim 1. Advantageous structuring of the invention is the subject of the subordinate claims.

The basic idea of this invention accordingly consists in the appropriation, in accordance with an aspect of an endoscopic surgical instrument, comprising a preferably hose-shaped outside sleeve or jacket, in which a preferably likewise hose-shaped inside sleeve or jackets supported relatively displaceable, at whose distal end section a sleeve- or shaft-shaped instrument head is developed or mounted, which protrudes axially distal from the outside jacket when it is in its maximum advanced position. In the instrument head, an RF electrode is fixed electrically-insulated, whose electrical supply line is guided by the inside jacket and which electrode projects freely beyond the distal end of the instrument head in an axial direction. The instrument head in this case can be pulled back axially into the outside jacket to such an extent, that the complete RF electrode is located axially behind (in proximal direction) the distal end of the outside jacket, therefore surrounded completely by the outside jacket. Furthermore, at least one individual (or several) opening flush channel(s) is/are formed in the instrument head axially, as well as on both axial instrument head ends, which simultaneously represents the discharge opening for the flush medium from the surgical instrument, that is therefore moved together with the RF electrode axially and retains the relative position with respect to the RF electrode.

In this way, the flush jet can always be guided optimally with respect to the RF electrode, as a result of which the flush result is improved in total. Furthermore, since only one flush channel, viewed in the axial direction, must be passed through, the flow resistance reduces so that the flush pressure increases.

Basically, it is the case with this instrument that the RF electrode is fixed in the instrument head—therefore it cannot be moved axially relative to the head. Instead of this, the instrument head is slid axially within the outside jacket. The basic technical background to this construction is based on the following consideration:

The RF electrode must basically be exactly positionable in an advantageous manner, where it should be guided in a support: If, for example, an endoscope shaft is therefore considered as a component part of a surgical instrument inserted within it, and the instrument shaft would be set equal to the invention-related inside jacket, the endoscope shaft (and its distal end section) would then have to take over such a guiding function. However, it is the case with endoscopes and surgical instruments inserted in them, that an inside shaft (the surgical instrument) would be advanced unguided from the working channel of the endoscope in the distal direction. Such a "sloppy extension" of the instrument from the endoscope certainly would have a guiding quality which does not make it possible to position/guide the RF electrode by means of the endoscope shaft or the insertion aid. Expressed in other words, an endoscope shaft serves exclusively for inserting the surgical instrument into a hollow organ, then the surgical instrument is advanced out from the endoscope shaft axially and finally the RF pin/electrode is advanced freely, where this displacement within the surgical instrument is generally guided by an insert. This means that the RF pin/electrode must be supported/restricted radially.

It is known that this support is implemented by means of the insert fixed in the instrument sleeve (inside sleeve), which has a central transition hole into which the RF pin/electrode is inserted with a slide action. In case of this invention, however, it is exactly reversed. This means that, invention-related, the RF pin/electrode is seated in a central transition hole of a sliding block, namely the endoscope head, which is guided with a slide action on its outside radius on an outside jacket of the surgical instrument (probably being inserted into an endoscope being not subject matter of the present invention), and it also retains this sliding-guide contact in all working positions as described below by means FIG. 2. In addition, it is preferably planned that the instrument head, in an active position of the surgical instrument, is (only) in-part displaced from the hose-shaped outside jacket, and in addition still has sliding contact and thus continues to be guided.

Finally, it is preferably planned that, to avoid canting of the instrument head, the latter should be larger than the diameter of the outside sleeve in which it is guided with a slide action.

In this case, the sliding guide can be implemented fluid-sealed invention-related.

It is advantageous if the proximal flush channel opening ends directly in the interior compartment of the inside sleeve, in order to be subjectable with a flush medium conveyed by the inside jacket. The flow cross section can be enlarged by that within the instrument shaft (outside and inside jacket).

A further advantageous development of the invention provides that the instrument head is slidingly guided at the outside jacket, preferably fluid-sealed. As a result of this, additional support measures can be dispensed with, so that the overall construction of the surgical instrument is simplified.

An additional or alternative aspect of the existing invention provides that the sleeve-shaped instrument head has a distal axial section with large outer diameter as sliding guide at the outside jacket, and a proximal axial section with small outer diameter as a fluid-sealing insertion or screwed-on base socket for the inside jacket. As a result of this, the instrument head is provided with a pre-determined axial length, which enables a cant-free guiding within the outside jacket. This construction thus forms the prerequisite for the situation where no further slide support has to be provided, through which the flush medium must be routed.

It is advantageous if the preferably fluid-sealed fixing of the RF electrode is implemented in the instrument head by means of at least one clamp bushing, preferably two axially-separated clamp bushings which is/are located around the RF electrode and inserted plug-like into the sleeve-shaped instrument head. On the one hand, as a result of this, a sufficient fixing of the RF electrode with the instrument head is achieved and, on the other hand, the inside jacket is closed off fluid-sealed so that this is usable as a line for the flush medium.

As has already been suggested above, it is further advantageous if the sleeve-shaped instrument head can be subjected by an advance force applied as a driving force via the inside jacket and/or via the electrical supply line, in order to advance the RF electrode, and also at least partially the sleeve-shaped instrument head, from the distal end of the outside jacket and/or to withdraw it into the outside jacket to such an extent that the RF electrode in withdrawn position (including the free electrode tip) is proximally completely located behind the distal end of the outside jacket. In this withdrawn position, the RF electrode is thus enclosed completely by the outside jacket (of electrically-insulating material) and no organ tissue can be damaged.

FIGURE DESCRIPTION

The invention is explained in more detail in the following by means of a preferred design example, with reference to the accompanying drawings.

Figure 2:
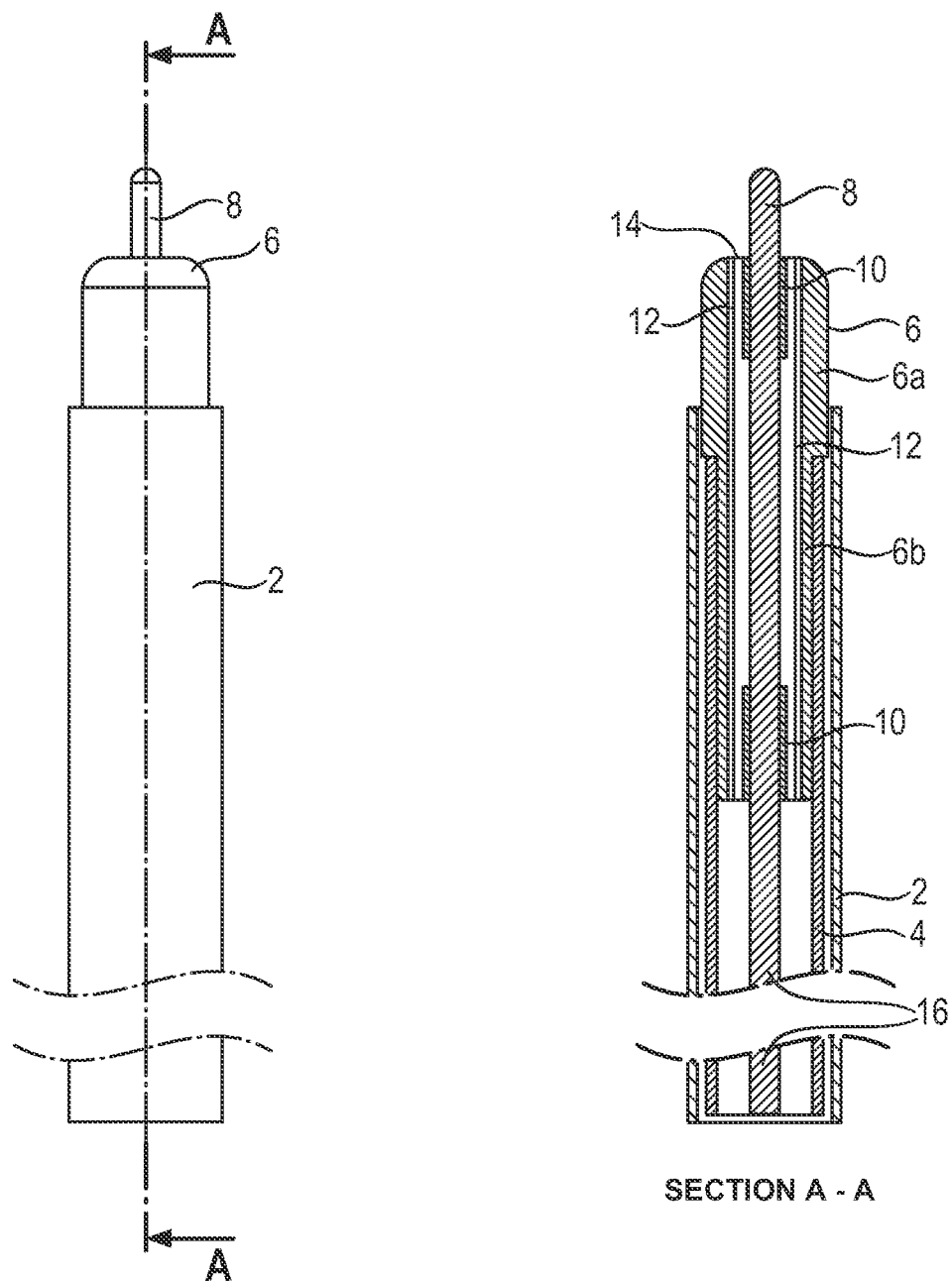
Figure 3:
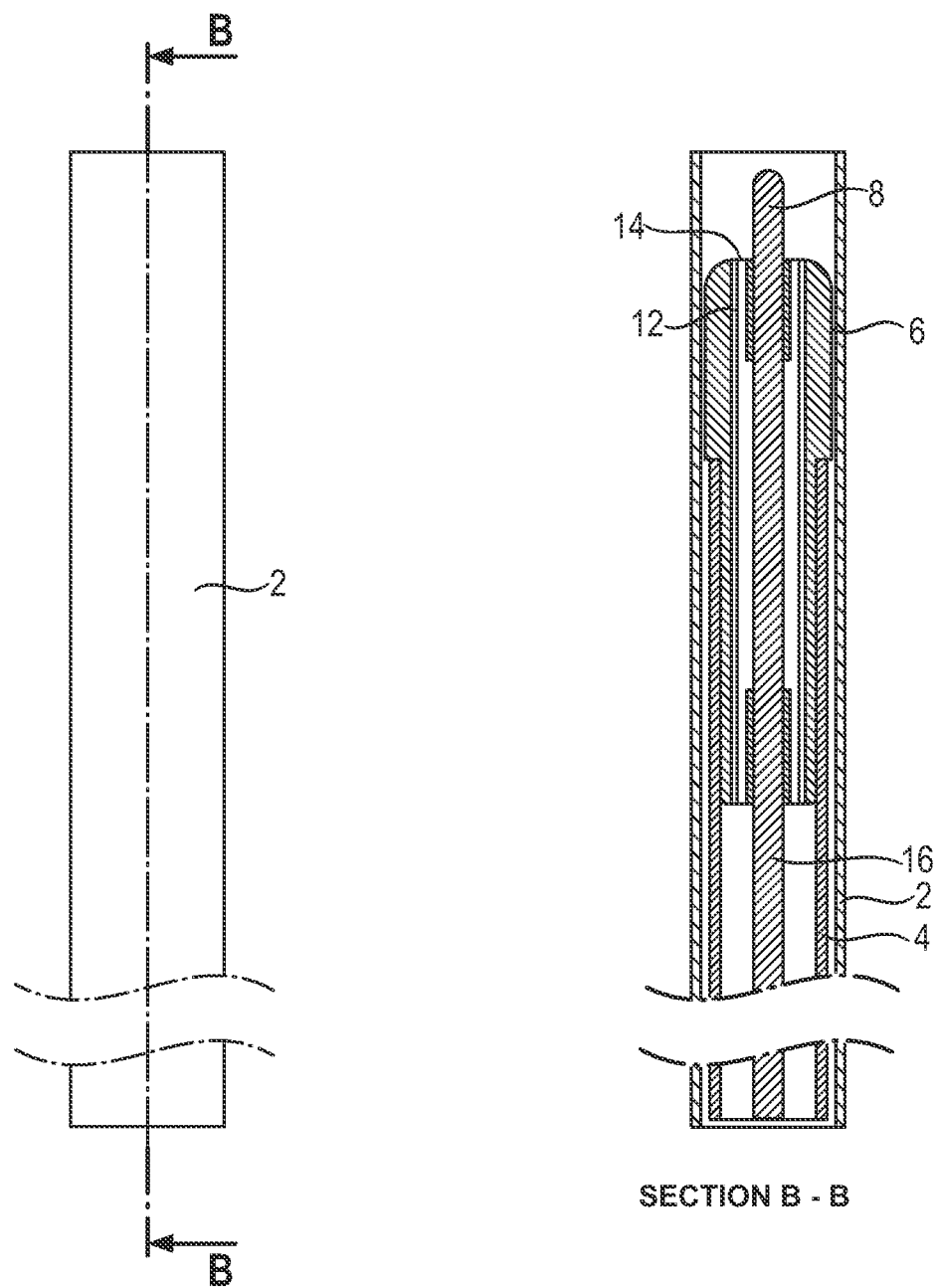

FIG. 1 shows the perspective view of a distal end section of an endoscopic surgical instrument of the TFT construction design, in accordance with a preferred implementation example of the invention, FIG. 2 shows the side, as well as corresponding longitudinal, section view of the distal end section in accordance with FIG. 1, in an activated (advanced) RF electrode position and FIG. 3 shows the side, as well as corresponding longitudinal, section view of the distal end section in accordance with FIG. 1, in a deactivated (advanced) RF electrode position.

In accordance with FIG. 1, the endoscopic surgical instrument of the TFT construction design of a preferred embodiment of the invention has a preferably bend-flexible shaft 1, on whose proximal end an instrument grip/handle or an actuation device (not further represented) is arranged. A functional property of the instrument shaft can be understood as "bend-flexible" in that it allows/enables the instrument to follow the turns of a hollow organ of preferably a human body, such as for example the intestine, the gullet, a blood vessel, etc. without deforming the hollow organ in an supererogatory way. This means that the stiffness of the instrument shaft should be less, at least in bend direction, than the organ tissue to be treated, so that, during penetration movement, basically it is not the hollow organ which is deformed/bent, rather the instrument shaft.

The instrument shaft 1 consists as presented of a hose-shaped (first) outside sleeve/jacket 2 (for example from a silicone or PVC material or another bio-compatible flexible material), in which a likewise hose-shaped (second, separate) inside sleeve/jacket 4 is axially guided, which can be produced from a similar or similar-type material. The outside and inside jacket 2, 4 can have an insertion for example of a tissue, a spiral or similar strengthening, in order to increase the stiffness in the axial direction with high bend flexibility and/or to reduce the widening capability in the case of an internal pressure rise.

At the distal end section of the surgical instrument as shown in FIG. 1, the inside jacket 4 has an instrument head 6, which axially closes off the interior compartment of the inside jacket 4 except for at least one flush channel (described below in greater detail) and which supports an RF electrode 8 (fixed) preferably centrally, which protrudes axially from the instrument head 6, in order to form an RF electrode cutting edge.

In FIG. 2 the invention-related surgical instrument is represented in side and longitudinal section. Accordingly, the instrument head 6 consists of a sleeve-shaped bolt or shaft piece preferably made of a ceramic material, with two axially-offset (adjacent) functional sections 6a, 6b of different outside diameters. A distal functional section 6a with large outside diameter is provided and adapted in order to slide at the inner side of the hose-shaped outside jacket 2. Accordingly, the outer diameter of the distal functional section 6a of the instrument head 6, with the formation of a small play (gap), is only slightly smaller than the inner diameter of the outside jacket 2, so that in the most favorable case even a sealing effect is achieved between the instrument head 6 and the outside jacket 2. A proximal functional section 6b with small outer diameter (with respect to the distal functional section 6a) is provided and adapted to enable it to be inserted distally as well as axially fluid-sealed (pressed in, bonded, screwed, etc.) into the hose-shaped inside jacket 4. The overall length of the instrument head (including sleeve-shaped bolt sections 6a and 6b) 6 is selected preferably so that, with an axial displacement along the outside jacket 2, it cannot cant in this or can do so with difficulty only. This means that the overall length of the instrument head (including sleeve-shaped bolt sections 6a and 6b) 6 is (considerably) greater than the diameter of the outside jacket 2.

The sleeve-shaped bolt form of instrument head 6 has a continuous, preferably central, axial bore into which an RF electrode 8 is inserted in such a way that this projects beyond the distal front side of the instrument head 6 by a predetermined length, and forms the RF electrode cutting edge in this case. In the concrete case, the RF electrode 8 is formed from electrically-conducting material by a wire or pin which is fixed in the axial bore of the instrument head 6, preferably at both axial bolt ends by means of clamp bushings 10 surrounding the wire 8, which are pressed into the axial bore for that. The instrument head 6 is further inserted axially as well as distal sealing in its proximal functional section 6b into the hose-shaped inside jacket 4, as this was already suggested above, wherein the inside jacket 4 is pulled over (extends over) the proximal functional section 6 b in the distal direction to such an extent that this contacts the distal functional section 6a (with greater outside diameter).

The sleeve-shaped bolt form of instrument head 6 furthermore has at least one, preferably a number of uniformly angular-separated axial through-holes (channels) 12, being arranged on a circular orbit surrounding the central RF electrodes 8 and which through-holes form flush channels. These flush channels 12 are opened at the proximal front side of the instrument head 6 into the interior compartment of the hose-shaped inside jacket 4, and form flush medium outlet openings (nozzles) 14 of the surgical instrument at the proximal front side of the instrument head 6. This means that these flush medium outlet openings 14 represent the distal most frontal (last) instrument flush openings, from where a flush medium (flush liquid) is sprayed directly onto an operation location/RF electrode. For that, this flush medium is pressed through the hose-shaped inside jacket 4 with predetermined pressure over the entire instrument shaft length.

As can be seen in FIG. 2, an electrical supply line 16 also runs within the hose-shaped inside jacket 4 for the optional application of an electric current on the RF electrode 8. The hose-shaped inside jacket 4 and/or the supply line 16 are additionally used in this case for the transfer of a pushing-/pulling force onto the instrument head, ultimately including the instrument head 6 and the RF electrode 8 fixed in that, in order to move the instrument head 6 and the RF electrode 8 along the hose-shaped outside jacket 2.

The functioning method of the invention-related surgical instrument is described below by means of FIGS. 2 and 3.

In FIG. 2 the invention-related surgical instrument is displayed in activated position. Accordingly, the instrument head 6, especially the freely protruding part of the RF electrode 8 (cutting edge section) in its entirety, and also the sleeve-shaped bolt distal functional section 6a at least partially protrude axially from the hose-shaped outside jacket 2. To avoid tissue injuries, the sleeve shaped bolt distal functional section 6a is rounded off at least in the area exposed to the outside. The discharge openings or spray openings 14 of the flush channels 12, together with the RF electrode 8 fixed in the instrument head 6, are moved distal wherein the flush channels 12 thus retain their relative location to the RF electrode 8, in particular its free electrode tip. In this way, the optimal flushing effect is always attainable in every axial position of the RF electrode 8 relative to the outside jacket 2.

In FIG. 3 the invention-related surgical instrument is represented in deactivated position. In this case, the instrument head 6 is completely withdrawn into the hose-shaped outside jacket 2 in the proximal direction, to such an extent that also the electrode tip is located (proximally) behind the distal leading edge of the outside jacket 2 and is thus completely enclosed/covered by this.

In this position, the RF electrode can no longer damage any organ tissue, also in case of unintentional application of electric current. In this position, the flush discharge openings 14 of the surgical instrument, together with the instrument head 6, are pulled back in proximal direction into the outside jacket 2 and can no longer be clogged up or contaminated by bodily liquids or tissue.

In summary, what is disclosed is an endoscopic surgical instrument (adapted to be inserted into an endoscope) with a hose-shaped outside jacket providing an instrument shaft 2, in which a likewise hose-shaped inside jacket 4 is supported relatively displaceable, on whose distal end section a sleeve or shaft-shaped instrument head 6 is developed or mounted. A pin or pin-shaped RF electrode 8 is preferably fixed in the instrument head 6 in an electrically insulated manner. The electrical supply line 16 to the electrode is routed along the inside jacket 4. The electrode 8 freely projects beyond the distal end of the instrument head 6 in an axial direction. Furthermore, in the instrument head 6 at least one (preferably several, uniformly angular-separated) flush channel 14 is formed extending axially, as well as being open at both instrument head ends, which forms at the distal end of the instrument head 6 the actual (distal last) flushing agent discharge opening of the surgical instrument for a flush agent/medium. Therefore, if the RF electrode 8 (necessary), in-part together with the instrument head 6, is axially shifted from the outside jacket 2 toward the front in the distal direction to the outside, the flush medium discharge opening 14 is displaced together with the RF electrode 8, so that the separation distance and the orientation between the at least one discharge opening 14 and RF (HF) electrode 8 remains unchanged. Thus a maximum flush result can be achieved in every advance position of the RF electrode 8 with respect to the outside jacket 2.

The invention claimed is:

1. An endoscopic surgical instrument comprising:
   an outside jacket;
   an inside jacket supported inside the outside jacket and displaceable relative to the outside jacket;
   a sleeve-shaped instrument head in a form of a bolt, the sleeve-shaped instrument head fixedly connected on a distal end section of the inside jacket, the sleeve-shaped instrument head further comprising a flush channel open at both axial ends of the sleeve-shaped instrument head, the flush channel further comprising an instrument flush medium opening at a distal end of the inside jacket proximate the sleeve-shaped instrument head;
   a radio frequency (RF) electrode included in the sleeve-shaped instrument head in an electrically-insulated manner;
   an electrical supply line for the RF electrode, the electrical supply line being routed within the inside jacket so that the sleeve-shaped instrument head, together with the RF electrode and electrical supply line, are displaceable in an axial direction beyond a distal end of the outside jacket without changing a relative position between the RF electrode and the instrument flush medium opening;
   wherein the RF electrode is immovably fixed in the sleeve-shaped instrument head in such a way that it freely projects in every relative operation position to the outside jacket in an axial direction beyond a distal end of the sleeve-shaped instrument head and that a distance between a distal end of the RF electrode and the distal end section of the inside jacket is invariable; and wherein the sleeve-shaped instrument head remains at least partially guided in the outside jacket in every relative operation position with respect to the outside jacket in a fluid-sealed manner.

2. The endoscopic surgical instrument according to claim 1, wherein a proximal flush channel ends directly in an interior compartment of the inside jacket in order to be subjectable with a flush medium conveyed by the inside jacket.

3. The endoscopic surgical instrument according to claim 1, wherein the sleeve-shaped instrument head has a distal axial section with an outer diameter which is larger than an inner diameter of the inside jacket, the distal axial section located directly at the outside jacket in a sliding manner, and further wherein the sleeve-shaped instrument head has a proximal axial section having an outside diameter which is smaller than the inner diameter of the inside jacket, the proximal axial section serving as a fluid-sealing insertion or screw-on base socket for the inside jacket.

4. The endoscopic surgical instrument according to claim 1, wherein a fluid-sealed fixing of the RF electrode within the sleeve-shaped instrument head is implemented by at least one clamp bushing that is located around the RF electrode and wherein the clamp bushing is plugged into the instrument head.

5. The endoscopic surgical instrument according to claim 1, wherein the sleeve-shaped instrument head consists of a ceramic material.

6. The endoscopic surgical instrument according to claim 1, wherein the outside and inside jackets consist of a bend-flexible material which is adapted to follow channel turns in human organs.

7. The endoscopic surgical instrument according to claim 1, wherein the sleeve-shaped instrument head is subjectable to an advancing force as a push-in and pull-out force via the inside jacket and the electrical supply line or only via the electrical supply line, in order to advance the RF electrode from the distal end of the outside jacket and/or to withdraw it into the outside jacket, to such an extent that it comes to rest completely proximal behind the distal end of the outside jacket, wherein relative movement of the outside and inside jackets is slidingly guided by the sleeve-shaped instrument head.

8. The endoscopic surgical instrument according to claim 1, wherein the sleeve-shaped instrument head is rounded off on an outside of the distal end section.

9. The endoscopic surgical instrument according to claim 1, wherein at least the inside jacket is formed hose-shaped, with an inner flexible material reinforcement, in order to resist an internal pressure caused by supplied flush medium.

10. The endoscopic surgical instrument according to claim 1, wherein to avoid canting of the sleeve-shaped instrument head, the sleeve-shaped instrument head is axially longer than a diameter of the outside jacket.

* * * * *